(12) United States Patent
Perez et al.

(10) Patent No.: US 7,344,890 B2
(45) Date of Patent: Mar. 18, 2008

(54) METHOD FOR DISCRIMINATING PLATELETS FROM RED BLOOD CELLS

(75) Inventors: Carlos A. Perez, Miami, FL (US);
Lidice L. Lopez, Miami, FL (US);
Mark A. Wells, Davie, FL (US);
Joaquin Ibanez, Cooper City, FL (US);
Eileen Landrum, Miami, FL (US);
Roberto Del Valle, Coral Gables, FL (US); Santiago Galvez, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 177 days.

(21) Appl. No.: 11/270,859

(22) Filed: Nov. 9, 2005

(65) Prior Publication Data
US 2007/0105230 A1   May 10, 2007

(51) Int. Cl.
*G01N 33/48*   (2006.01)
(52) U.S. Cl. ............................ 436/63; 436/8; 436/10; 436/17; 436/164; 436/174; 436/175; 422/73; 422/82.05; 422/82.09; 435/2
(58) Field of Classification Search .................... 436/8, 436/10, 17, 63, 164, 174, 175; 422/73, 82.05, 422/82.09; 435/2
See application file for complete search history.

(56) References Cited

U.S. PATENT DOCUMENTS

| 4,577,964 | A | | 3/1986 | Hansen |
| 5,616,501 | A | | 4/1997 | Rodriguez et al. |
| 5,817,519 | A | * | 10/1998 | Zelmanovic et al. ......... 436/63 |
| 6,114,173 | A | * | 9/2000 | Zelmanovic et al. ......... 436/63 |
| 6,228,652 | B1 | * | 5/2001 | Rodriguez et al. ............ 436/63 |
| 6,869,569 | B2 | * | 3/2005 | Kramer ....................... 422/73 |
| 2003/0030783 | A1 | | 2/2003 | Roche et al. |
| 2004/0121484 | A1 | | 6/2004 | Betancourt et al. |
| 2007/0105231 | A1 | * | 5/2007 | Riley et al. ................... 436/63 |

OTHER PUBLICATIONS

Kunicka et al. American Journal of Clinical Pathology, vol. 114, 2000, pp. 283-289.*

* cited by examiner

*Primary Examiner*—Maureen M. Wallenhorst
(74) *Attorney, Agent, or Firm*—Cuspa Technology Law Associates; Mitchell E. Alter

(57) ABSTRACT

A method for discriminating and quantifying platelets within an analyzed blood sample involves initially diluting the blood sample with a ghosting reagent that causes a change in the index of refraction of the red blood cells. Owing to the change in the index of refraction, light scattered from the ghosted red blood cells will be substantially reduced relative to light scattered from platelets. This results in locations of platelets within a scatterplot of the analyzed blood sample to fall within a region distinguishable from those containing normal red blood cells, fragmented red blood cells, and microcytic red blood cells.

12 Claims, 3 Drawing Sheets

US 7,344,890 B2

METHOD FOR DISCRIMINATING PLATELETS FROM RED BLOOD CELLS

FIELD OF THE INVENTION

The present invention relates to a method and instrument system utilizing light scatter technology without the utilization of fluorescent staining techniques or materials for differentiating and enumerating platelets from erythrocytes or red blood cells (including microcytes and fragmented red blood cells), as well as from oversized or giant platelets and platelet aggregates or clumps.

BACKGROUND OF THE INVENTION

Clinical instruments currently in use for analyzing the components of a blood sample employ a wide variety of electrically and optically based techniques to discriminate and quantify platelets from other cells or particles, such as red blood cells, including normal red blood cells and microcytic red blood cells, red blood cell fragments, oversized platelets and platelet aggregates.

A measurement utilizing monoclonal antibodies which bind specifically to platelet cells is widely recognized as the most accurate method, even in the presence of interfering substances, such as platelet clumps, giant or oversized platelets, microcytic red blood cells and red blood cell fragments. Preparation of the sample for this method requires multiple dilutions and incubation periods that can range to well over ten minutes. To collect emitted optical signals created by this method, in addition to forward light scatter measurements, this method requires the optical means to collect the fluorescent light and highly sensitive sensors, such as PMTs, to accurately measure the fluorescent signal. The expense associated with this hardware is prohibitive with low cost instrumentation. In addition, long incubation periods are not favorable for instruments with high sample throughput requirements. An additional drawback to monoclonal antibodies is the relative expense of the reagent.

A second method that has been recognized to provide accurate platelet enumeration is that of treating the blood specimen with a fluorescent dye and identifying the platelet cell by a fluorescence measurement. Although this method typically does not require extended incubation periods and the dye reagent is relatively inexpensive compared to monoclonal antibodies, there is an additional expense associated with the hardware to perform this measurement. Moreover, some dyes are associated with non specific binding to various cell types.

Other methods exist which identify platelet cells by means of a strictly optical measurement. Various disadvantages are associated with these methods. First, all of these methods require multiple sensors, adding complexity and expense to their respective instruments. Additionally, these methods have limitations discriminating red blood cells from platelet cells in the presence of interfering substances.

There are several methods known to those skilled in the art for utilizing light scatter for identification of white blood cells. Moreover, U.S. Pat. No. 5,616,501 teaches a method of determining reticulocytes in a blood sample by using a ghosting reagent and preferably an RNA precipitating dye with light scatter measurements.

Hansen U.S. Pat. No. 4,577,964, discloses a method which utilizes low angle light scatter measurement and pulse duration to discriminate platelet cells from red blood cells in a diluted blood specimen. Inherent in this method is the fact that, although the blood sample is diluted, red blood cells and platelet cells maintain their respective volumes and the measurement is based upon their optical characteristics. In other words, cells in the diluted sample maintain their native states. This method provides the advantage of a single optical sensor for the light scatter measurement and an electronic measurement derived from the light scatter signal for the pulse duration. Although providing relatively accurate and precise platelet enumeration for normal samples without interfering substances, limitations exist for discriminating red blood cells from platelets in the presence of interfering substances such as platelet clumps.

Recent advances in technology have demonstrated improvements in the measurement of pulse width, or time-of-flight measurements. This method collects a broad angle forward light scatter signal and calculates a time-of-flight value for each blood cell event from a diluted blood specimen. The buffer solution maintains the red blood cells and the platelet cells in their native states. As shown in the scatterplot of FIG. 1, this method yields an accurate and precise platelet enumeration, region 11, for normal samples without interfering substances. Region 12 corresponds to the RBC population and region 13 corresponds to the RBC coincidence. However, this method is still subject to limitations in the presence of interfering substances such as in FIG. 3 region 31 (giant platelets or oversize platelets), FIG. 5 region 51 (platelet clumps or aggregates), and FIG. 7 region 71 (RBC fragments).

For example, in some cases, the volume of platelet clumps and oversized platelets tends to approach that of a normal red blood cell population. Consequently, their light scatter signal often overlaps a portion of the red blood cell population thereby preventing proper identification of the platelet cells, as shown at region 21 in the scatterplot of FIG. 2, and region 41 in the scatterplot of FIG. 4. (The scatterplot of FIG. 3 corresponds to that of FIG. 2 with the red blood cells removed from region 31, while the scatterplot of FIG. 5 corresponds to that of FIG. 4, with the red blood cells removed from region 51.) This condition often results in the platelet population being under counted.

Conversely, the volume of microcytic red blood cells and red blood cell fragments can approach that of normal platelet cells thereby causing their scatter signal to overlap that of platelet cells, as shown at region 61 in the scatterplot of FIG. 6. (FIG. 7 corresponds to the scatterplot of FIG. 6, with the platelets removed from region 71.) Not being distinguished from the platelets, these red blood cells are counted as platelets causing the platelet population to be over counted.

In addition to potential interferences from abnormal red blood cell and platelet populations, normal white blood cells may also tend to exhibit the same or similar light scatter and pulse duration measurement results as those of red blood cells. In normal samples, the ratio of red blood cell to white blood cells is typically about a thousand to one. Consequently, overlap between red blood cells and white blood cells imparts minimal impact to the red blood cell or platelet counts. However, certain medical conditions, such as severe infection or leukemia, cause elevated levels of white blood cells. Furthermore, conditions such as anemia or excessive bleeding cause a substantial decrease in the levels of red blood cells. Either of these types of conditions, or a combination of these types of conditions results in an inaccurate estimation of the red blood cell count, which in turn results in an inaccurate estimation of the platelet count.

SUMMARY OF THE INVENTION

The present invention relates to a method of differentiating platelet from red blood cells in a blood cell sample comprising the steps of (a) combining a blood cell sample containing red blood cells and platelet cells with a ghosting reagent to form a blood cell sample suspension, said ghosting reagent being effective to modify the index of refraction of the red blood cells within the blood cell sample suspension; (b) flowing said blood cell sample suspension through a particle sensing zone of an instrument; (c) directing a light beam through said particle sensing zone to intersect the cells contained in the blood cell sample suspension; (d) detecting light scattered by the cells that pass through the particle sensing zone; and (e) analyzing the light scattered by the cells to differentiate red blood cells from platelet cells. In a preferred embodiment, the method further comprises enumerating the platelet that are differentiated from the red blood cells. In both method embodiments described above, the blood cell sample comprises whole blood.

In a further embodiment, the present invention comprises an improvement in a method of analyzing a blood sample by way of a cell analyzer, wherein a suspension containing said blood sample flows through a transport path of said automated hematology analyzer, and a light beam is directed through said transport path of said automated hematology analyzer, thereby causing light to be scattered by blood sample cells passing through said transport path of said automated hematology analyzer, and wherein a scatterplot of said blood sample cells is generated in accordance with characteristics of said light as scattered by said blood sample cells and detected by a scattered light detector, wherein the improvement comprises adding to the suspension a prescribed reagent that is effective to modify the index of refraction of said non-platelet cells within said suspension, and thereby cause light scattered by said non-platelet cells to be different from light scattered by said platelets, such that locations of platelets within said scatterplot fall within a region apart and readily distinguishable from those containing said non-platelet cells.

In a further embodiment, the scatterplot comprises a distribution of amplitudes of said light as scattered by blood sample cells with respect to the cells time of flight in the sensing zone.

DETAILED DESCRIPTION

Figure 9:
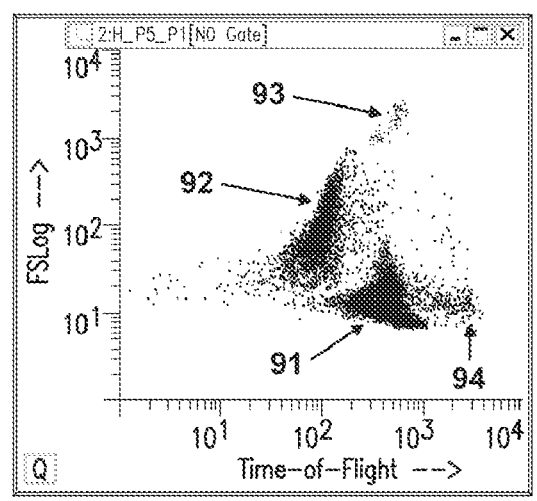
FIG. 9 is a scatterplot of forward scatter vs. time-of-flight of an analyzed blood sample that has been diluted with a ghosting reagent in accordance with the present invention, resulting in a modification of the index of refraction of the red blood cells, so that the platelet population is readily distinguished from red blood cells, microcytic red blood cells and red blood cell fragments.

In accordance with the present invention, shortcomings of conventional techniques, including those described above, to discriminate and quantify platelet cells within an analyzed blood sample, are effectively obviated by pre-treating (diluting) a blood cell sample to be analyzed with a ghosting reagent that causes a changing of the index of refraction of the red blood cells. As illustrated in FIG. 9, as a result of this change in the index of refraction of the red blood cells, light scattered from the red blood cells, region 91, is markedly different from (reduced relative to) light scattered from platelets, region 92. The difference in light scattering properties of the treated red blood cells and platelets causes the locations of normal platelets within a scatterplot of the analyzed blood cell sample to fall within a region apart and readily distinguishable from those containing normal and abnormal red blood cells, including fragmented and microcytic red blood cells, and oversized and aggregate platelets.

As noted above, the shift in the location of the ghosted red blood cell population is away from a region that normally overlaps oversized and aggregate platelets. This effectively leaves a gap between the upper end of the normal platelet population and the populations of oversized platelets and platelet aggregates. It is noted that the populations of oversized platelets and platelet aggregates tend to exhibit increased scatter intensity relative to ghosted red blood cells, and thereby move away from the red blood cell population region to a different region which is well above the red blood cell population region. In addition, the populations of oversized platelets and platelet aggregates appear to move upwards and to the right of platelet distribution region, so as to facilitate gating of the platelet population from the RBG population.

However, the WBC population in FIG. 9 region 93 may cause interference in the presence of oversized platelets and aggregate platelets. If there is WBC/platelet interference, then all WBC events can be included as part of the platelet count. In such case, the platelet count is corrected by subtracting the absolute WBC count of the same sample analyzed in the hematology instrument system.

On the other hand, microcytic red blood cells and red blood cell fragments exhibit a decreased light scatter relative to normal red blood cells. The distribution of such reduced size red blood cell components lies at the bottom of the ghosted red blood cell population, as shown by region 91, which is well separated from the platelet population region 92. Region 94 corresponds to the RBC coincidence.

As previously described, when the blood sample is combined with the ghosting reagent, the ghosting reagent interacts with the red blood cells to cause a substantial change in the optical characteristics of the red blood cells. More specifically, the index of refraction of the red blood cells in the blood cell sample are changed, such that the amplitude of the measured light scatter from ghosted red blood cells will be substantially different (lower) than that of unghosted cells and most platelets. The change in the index of refraction of the red blood cells is due to a loss of hemoglobin, which is an effect that is commonly referred to as 'ghosting' of the red blood cells. However, the ghosting reagent does not affect the platelets the same way so that the platelets do not form ghosts. This causes the locations of red blood cells within a scatterplot of the analyzed blood sample to fall within a region apart and distinguishable from those containing platelets.

An example of a ghosting reagent that can be utilized to differentiate and enumerate the platelets comprises potassium thiocyanate and sulfuric acid. This type of ghosting reagent can be obtained as a commercial product known as Reagent B of the Coulter Retic Pak™ P/N 8547115. Other ghosting reagents known to those skilled in the art can be used in this invention.

Typically, the ghosting reagent is in an amount sufficient to effectively swells the red blood cell to a spherical shape without bursting them and to permit hemoglobin to leak from the red blood cells.

In the present method, there is an absence of a dye or a stain used to obtain an index of refraction. More particularly, a dye or stain is not required to provide a difference in the index of refraction between the cells and platelets; however, in an alternate embodiment, one can further use a dye to enhance the index of refraction difference between the cells and platelets. Such dyes are known to those skilled in the art to have cellular uptake within forty five (45) seconds of being mixed with a blood cell sample suspension formed from red blood cells and platelet cells mixed with a ghosting reagent.

It has been found that the ghosting process is affected by temperature. More specifically, it has been determined that temperatures below 55 degrees F. appear to retard the ghosting process and longer time periods are necessary to permit the ghosting process to occur. As a result, it is preferred that the blood cell sample be mixed with the ghosting reagent at a temperature of approximately 55 degrees to approximately 106 degrees F. for approximately 30 seconds. It has been determined that 106 degrees F. (41 degree C.) provides the shortest time of ghosting.

The pH of the ghosting reagent should be approximately 1.0 to 3.0, preferably 1.0 to 2.0. In addition, it appears that the acidic ghosting reagent solubilizes the hemoglobin and facilitates its removal from the blood cell. It has been noted that when utilizing potassium thiocyanate, sulfuric acid is the preferred acid to be utilized in the combination. More specifically, other acids which did not work as well as sulfuric acid, include hydrochloric and nitric acids. The preferred concentration for the potassium thiocyanate is approximately from 1.0 to 6.0 grams per liter, and for the sulfuric acid is approximately from 0.7 to 3.0 grams per liter.

The osmotic pressure of the ghosting reagent should be controlled so that there is a rapid, but controlled swelling of the red blood cell. The osmotic pressure of the ghosting reagent ranges from 75 to 110 milliosmoles, and preferably 82 to 105 milliosmoles. The osmotic pressure causes the red blood cell to swell and release hemoglobin within thirty (30) seconds of mixing with the ghosting reagent. If the osmotic pressure is less than 75 milliosmoles, then the red blood cell will not retain an intact cell membrane and will lyse. More specifically, lower osmotic pressure results in red blood cells that are damaged so that the differentiation between platelets and red blood cells will be affected. If the osmotic pressure is not within the desired range, the red blood cells will retain hemoglobin which will obscure platelet differentiation and enumeration. Moreover, platelet enumeration is typically reported as the RBC Ratio method, as described hereinafter. Consequently, preservation of red blood cells is preferred.

Figure 1:
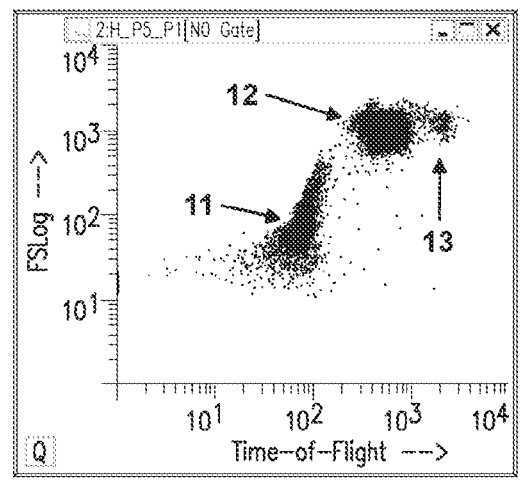
FIG. 1 is a scatterplot of forward light scatter vs. time-of-flight showing distributions of platelet and red blood cell populations of an analyzed normal blood sample, containing no interfering substances.
Figure 2:
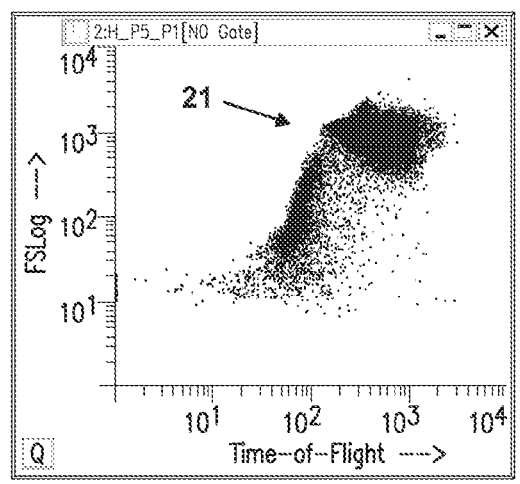
FIG. 2 is a scatterplot of forward light scatter vs. time-of-flight showing distributions of platelet and red blood cell populations of an analyzed blood sample, with oversized platelets overlapping the red blood cell population region.
Figure 3:
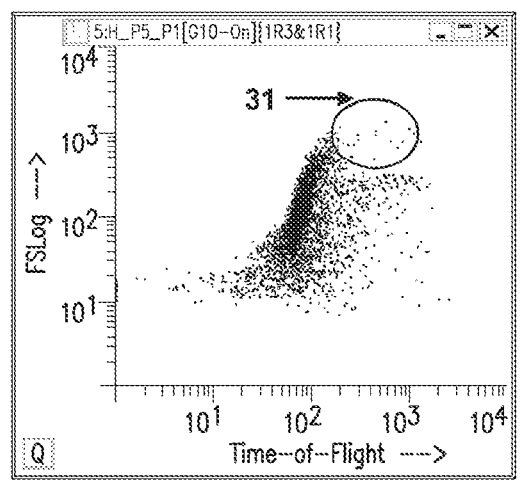
FIG. 3 is a scatterplot of forward light scatter vs. time-of-flight showing distributions of platelet and red blood cell populations of an analyzed blood sample as shown in FIG. 2, but with red blood cells removed by gating all RBC positive events using Glycophorin A monoclonal antibody.
Figure 4:
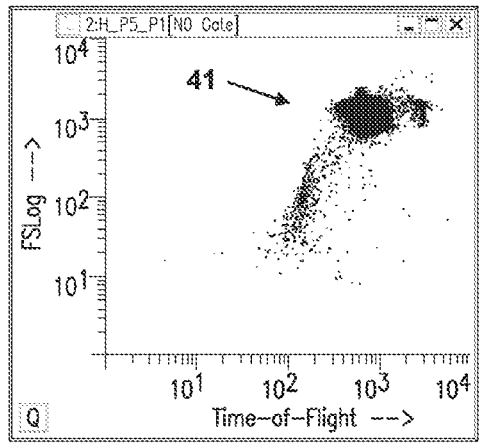
FIG. 4 is a scatterplot of forward light scatter vs. time-of-flight showing distributions of platelet and red blood cell populations of an analyzed blood sample, with platelet aggregates overlapping the red blood cell population region.
Figure 5:
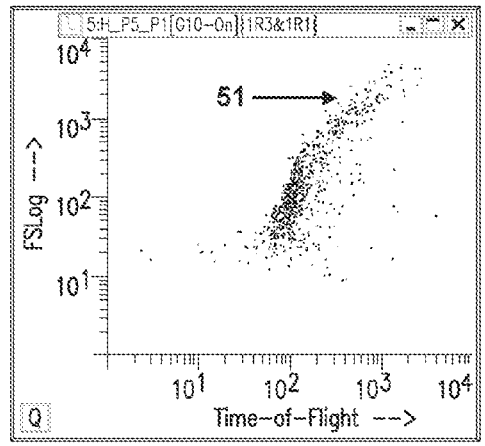
FIG. 5 is a scatterplot of forward light scatter vs. time-of-flight showing distributions of platelet and red blood cell populations of an analyzed blood sample as shown in FIG. 4, but with red blood cells removed by gating all RBC positive events using Glycophorin A monoclonal antibody.
Figure 6:
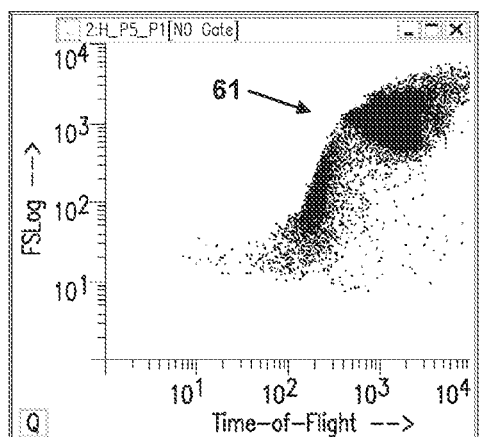
FIG. 6 is a scatterplot of forward light scatter vs. time-of-flight showing distributions of platelet and red blood cell populations of an analyzed blood sample, in which the number of microcytic red blood cells and red blood cell fragments approaches that of normal platelets, causing their scatter population to overlap the platelet population.
Figure 7:
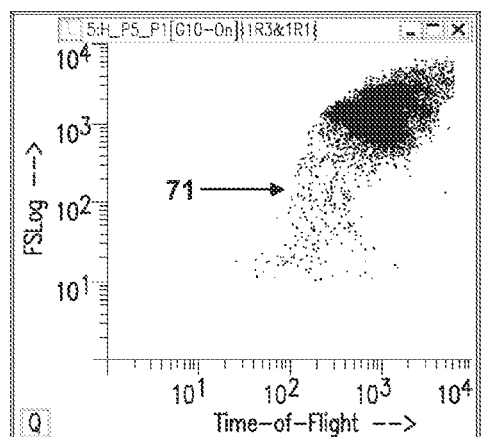
FIG. 7 is a scatterplot of forward light scatter vs. time-of-flight showing distributions of platelet and red blood cell populations of an analyzed blood sample as shown in FIG. 6, but with platelets removed by gating all platelet positive events using CD41/61 monoclonal antibody.
Figure 8:
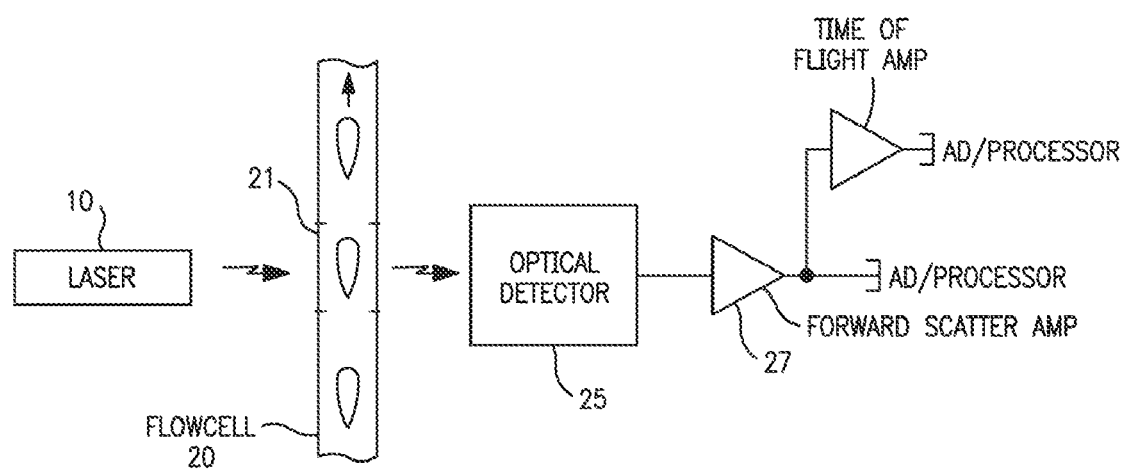
FIG. 8 is a block diagram of the overall architecture of an automated optically-based hematology system employed by the present invention to analyze a blood sample.

As shown in FIG. 8, the instrument system comprises an illumination source 10, such as a HeNe laser, which is operative to produce an output optical beam that is directed at (i.e. focused upon) an illumination aperture or window 21 of a flowcell 20, through which a carrier or sheath fluid containing a blood sample to be analyzed is hydrodynamically supplied. As described previously, pursuant to the invention, the blood sample supplied to the flowcell 20 is one that has been combined with a ghosting reagent.

As further shown in FIG. 8, spatially positioned relative to the illumination aperture of the flowcell 20 are one or more opto-electronic sensors 25 (such as photodiodes) that are operative to collect individual angular ranges of scattered light, such as but not limited to forward angle light scatter, side scatter (orthogonal) and backscatter.

For purposes of providing a non-limiting example, sensors 25 are shown as being positioned to detect forward scatter from particles or cells passing through the flowcell within a sheath fluid. The light scatter signals can be detected by photosensors at various angles relative to the incident light beam between 0 degree to 180 degrees. In the present invention, the light scatter signals detected are less than 20 degrees, preferably from 1 to 19 degrees, and most preferably from 2 to 16 degrees, from the incident light.

As further shown in FIG. 8, the electrical outputs of the photosensors 25 are coupled to associated electronic amplifiers 27, which produce output signals in the form of pulses, the amplitudes of which are proportional to (forward) scattered light intensity and the widths (or times of flight) of which are representative of the dimensional lengths of the cells or particles that give rise to the scattered light as the particles/cells within the carrier or sheath fluid traverse the illumination window of the flowcell.

Based upon the detected values of pulse amplitude and width, a two-dimensional scatterplot of forward scatter vs. time-of-flight or pulse width of each particle analyzed by the system is generated. An example of such a scatterplot is shown in FIG. 9. In particular, FIG. 9 is a scatterplot of forward scatter vs. time-of-flight of a blood sample that has been treated with a ghosting reagent, as described above, for the purpose of modifying the index of refraction of the red blood cells. As shown in FIG. 9, the effect is to cause the red blood cell population, denoted by region 91 to lie below and to the right of the platelet population 92. This shift in location of the red blood cell population as a result of the introduction of the ghosting reagent is in marked contrast to the location of the red blood cell population of a blood cell sample that has not been treated with a ghosting reagent, as shown in FIGS. 1, 2, 4, 6 and 7, referenced above.

Analyzers which do not have the ability to quantitatively measure the sample mixture through a flow cell compute the platelet count value by using the RBC-Ratio method. The RBC-Ratio method generates a platelet count by dividing the number of platelet events by the number of RBC events, and multiplying the results by an absolute RBC count from the same sample analyzed on a hematology system, producing an absolute platelet count ($n \times 10^3$ cells/µL).

Typically, the present method will have an absence of synthetic or natural particles; however, another method to obtain a quantitative measure of the platelet count is to use synthetic or natural particles, such as latex beads. More specifically, the method would comprise determining a total number of cells per volume of a cell specimen comprising the steps of (a) mixing a known quantity of particles having a first light scatter signal with a known volume of a cell specimen having a second light scatter signal different from the first light scatter signal to obtain a suspension having a concentration of particles per specimen volume, (b) passing each of said particles and cells in an unknown volume portion of said cell suspension, in turn, through a light beam, each of said particles and cells producing at least one forward light scattering signal, (c) counting the number of cells and the number of particles in said unknown volume portion of said suspension by using a flow cytometer, and (d) determining the total number of cells per volume of the specimen by correlating the number of particles and cells in said portion of the suspension to the known quantity of particles added to said cell specimen using light scatter measurements.

The invention has been described with reference to particularly preferred embodiments. It will be appreciated, however, that various changes can be made without departing from the spirit of the invention, and such changes are intended to fall within the scope of the appended claims. While the present invention has been described in details and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of differentiation of platelets in a blood cell sample comprising:
   (a) mixing a blood cell sample with a ghosting reagent to form a blood cell sample suspension, causing leaking of hemoglobin from red blood cells in said suspension and a reduction of light scattered by said red blood cells relative to light scattered by platelets;
   (b) flowing said suspension through a particle sensing zone of an instrument;
   (c) directing a light beam at said particle sensing zone;
   (d) measuring intensities of light scatter signals of said platelets and non-platelet cells in said suspension passing through said particle sensing zone, and time-of-flight of said platelets and said non-platelet cells in said particle sensing zone; and
   (e) analyzing said intensities of said light scatter signals and said time-of-flight of said platelets and said non-platelet cells to differentiate said platelets from said non-platelet cells.

2. The method of claim 1, wherein said analyzing said intensities of said light scatter signals and said time-of-flight is performed on a two-dimensional scatterplot of said intensities of said light scatter signals vs. said time-of-flight of said platelets and said non-platelet cells.

3. The method of claim 2 further comprising enumerating said platelets.

4. The method of claim 3, wherein said light scatter signals are detected at less than 20 degrees from the incident light.

5. The method of claim 4, wherein said blood cell sample comprises whole blood.

6. The method of claim 5, wherein said non-platelet cells comprise red blood cells including fragmented red blood cells and microcytic red blood cells.

7. The method of claim 6, wherein said light scatter signals of said fragmented red blood cells and microcytic red blood cells in said blood cell sample suspension have lower intensities than said light scatter signals of said platelets.

8. The method of claim 7, wherein said platelets include normal platelets, giant platelets and platelet aggregates.

9. The method of claim 8, wherein said light scatter signals of said giant platelets and platelet aggregates in said blood cell sample suspension have higher intensities than said light scatter signals of said red blood cells.

10. The method of claim 9 further comprising subtracting a white blood cell count of said blood cell sample from enumerated platelets to obtain a corrected platelet count.

11. The method of claim 10 further comprising differentiating white blood cells from red blood cells in said blood cell sample suspension.

12. The method of claim 2, wherein said method does not expose said blood cell sample to a dye or stain.

* * * * *